United States Patent [19]

Zebehazy

[11] Plant 5,224

[45] Apr. 24, 1984

[54] LEUCOTHOE PLANT—ZEBEKOT VARIETY

[75] Inventor: Alex J. Zebehazy, Perry, Ohio

[73] Assignee: Conard-Pyle Company, West Grove, Pa.

[21] Appl. No.: 276,061

[22] Filed: Jun. 22, 1981

[51] Int. Cl.[3] ..... A01H 5/00
[52] U.S. Cl. ..... Plt./54
[58] Field of Search ..... Plt./54

*Primary Examiner*—Robert E. Bagwill

*Attorney, Agent, or Firm*—Burns, Doane, Swecker & Mathis

[57] ABSTRACT

A new and distinct variety of Leucothoe is provided. While the new variety is believed to have resulted from the cross-pollination of *Leucothoe fontanesiana* with pollen from *Leucothoe axillaris,* this cross cannot be confirmed. The new variety is low growing and spreading and possesses narrower, more lanceolate leaves than other varieties which are believed to have originated from the same cross.

1 Drawing Figure

SUMMARY OF THE INVENTION

My invention relates to a new, distinctive and useful form of Leucothoe plant which was originated by me at Perry, Ohio. A breeding program was carried out whereby plants of *Leucothoe fontanesiana* were pollinated with pollen from plants which were purchased as being *Leucothoe axillaris*. However, there is the possibility that the pollen parent may have actually been *Leucothoe fontanesiana* var. *nana.* Also, following the attempted pollen transfer, the flowers of the seed parent were not bagged thereby making possible the introduction of pollen from an unknown source.

The object of my breeding was to create a colorful new variety of Leucothoe which combined the hardiness of *Leucothoe fontanesiana* with the attractive dwarf growth habit of *Leucothoe axillaris,* and which exhibited improved foliage coloration and an improved plant habit over both parents. This objective was achieved, along with other improvements, and the new variety exhibits a combination of characteristics which distinguish it from all other seedlings of this parentage and all other forms of Leucothoe of which I am aware.

The following combination of characteristics is exhibited by the new variety:

(a) a dense, low-growing symmetrical habit of growth which is more low-growing and compact than that of the *Leucothoe fontanesiana* and *Leucothoe axillaris* parents, as well as the Zeblid (U.S. Ser. No. 161,870, filed June 23, 1980) and Zebonard (U.S. Ser. No. 276,062, filed concurrently herewith) varieties of the same cross, (b) highly unique winter coloration which ranges from emerald green to a very slightly bronzed shade of green making the new variety an outstanding source of color in the landscape year-round, (c) outstanding tolerance to shade making the new variety an important addition to that small group of plants that does well in reduced sunlight, (d) the substantial absence of dead branches which are commonly found with *Leucothoe fontanesiana,*

(e) increased tolerance to cold when compared to *Leucothoe axillaris,* as is evidenced by the fact that the new variety has survived temperatures of −15° F. with little to no damage, whereas *Leucothoe axillaris* is listed as hardy to 0° F., and (f) foliage which is considerably narrower and more lanceolate than that of the Zeblid and Zebonard varieties of the same cross.

Asexual reproduction by cuttings of my new variety has been accomplished at Perry, Ohio, and at West Grove, Pa. Succeeding propagations have shown the unique combination of characteristics is fully established and is transmitted to successive generations.

The new variety has been named the Zebekot variety.

BRIEF DESCRIPTION OF THE PHOTOGRAPH

The accompanying photograph shows a typical specimen of my new variety of Leucothoe during late May as depicted in color as true as is reasonably possible to make the same in a color photograph of this character. The specimen shown in the photograph is a three year old plant growing in the ground at West Grove, Pa., which is approximately 24 inches in width and approximately 16 inches in height.

DETAILED DESCRIPTION

The following is a detailed description of my new variety made from the observation of three year old plants growing in the ground at West Grove, Pa. Color terminology is in accordance with The R.H.S. Colour Chart of The Royal Horticultural Society, London, England.

Parentage: *Leucothoe fontanesiana* × *Leucothoe axillaris.*

Foliage:

*Type.*—Evergreen. The leaves are basically lanceolate, and are noticeably more lanceolate than those of the Zeblid and Zebonard varieties of the same cross. The Zeblid variety is described in U.S. plant patent application Ser. No. 161,870, filed June 23, 1980, and the Zebonard variety is described in U.S. plant patent application Ser. No. 276,062, filed June 22, 1981. Apex acuminate, base obtuse, margins serrulate.

*Size of fully expanded mature leaves.*—From approximately 6.1 to 10.0 cm, in length, with an average of approximately 7.7 cm.; width from approximately 1.6 to 3.2 cm., with an average of approximately 2.1 cm. Petiole length from approximately 0.4 to 0.9 cm. Internode length from approximately 1.5 to 2.1 cm.

*Color.*—Immature leaves in May, upper surface — closest to but slightly darker than Yellow-Green Group 144A with tones of crimson at the leaf margins. Mature leaves in May, upper surface — Yellow-Green Group 147A; under surface — closest to Yellow-Green Group 146C. Mature leaves in winter, upper surface — closest to but slightly darker than Yellow-Green Group 147A with overtones of Greyed-Purple Group 183B.

Rate of growth: Average height and breadth of mature two year old plants is approximately 8 inches and approximately 15 inches, respectively.

*Flowers.*—The flowers and racemes of the present variety appear in May and more closely resemble those of *Leucothoe axillaris* than those of *Leucothoe fontanesiana*. The raceme length for the new variety commonly averages approximately 1.5 to 3.0 cm., and the raceme length for *Leucothol fontanesiana* is often twice this length. The individual flowers of the new variety are broadly ovate in shape, have an average length of approximately 6 to 7 mm., have an average base width of approximately 4 to 5 mm., and have an average apex width of approximately 3 mm. or less.

I claim:

1. A new and distinct variety of Leucothoe, substantially as herein shown and described, characterized particularly as to novelty by the unique combination of:

(a) a dense, low-growing symmetrical habit of growth which is more low-growing and compact than that of the *Leucothoe fontanesiana* and *Leucothoe axillaris* parents, as well as the Zeblid and Zebonard varieties of the same cross, (b) highly unique winter coloration which ranges from emerald green to a very slightly bronzed shade of green making the new variety an outstanding source of color in the landscape year-round, (c) outstanding tolerance to shade making the new variety an important addition to that small group of plants that does well in reduced sunlight, (d) the substantial absence of dead branches which are commonly found with *Leucothoe fontanesiana,*

(e) increased tolerance to cold when compared to *Leucothoe axillaris,* as is evidenced by the fact that the new variety has survived temperatures of −15° F. with little to no damage, whereas *Leucothoe axillaris* is listed as hardy to 0° F., and (f) foliage which is considerably narrower and more lanceolate than that of the Zeblid and Zebonard varieties of the same cross.

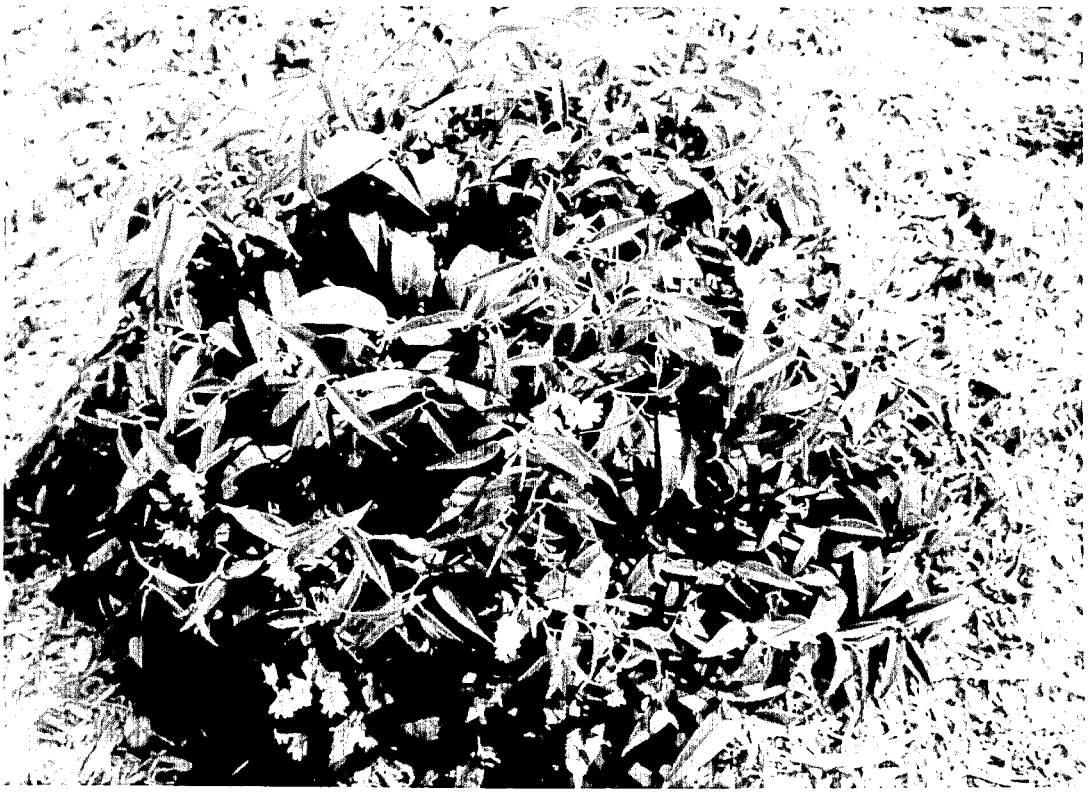

* * * * *